United States Patent
Noji et al.

(10) Patent No.: US 12,196,654 B2
(45) Date of Patent: Jan. 14, 2025

(54) MICROSCOPIC BODY DETECTION METHOD AND MICROSCOPIC BODY DETECTION DEVICE

(71) Applicant: JAPAN SCIENCE AND TECHNOLOGY AGENCY, Kawaguchi (JP)

(72) Inventors: Hiroyuki Noji, Tokyo (JP); Takao Ono, Osaka (JP); Yoshihiro Minagawa, Tokyo (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 584 days.

(21) Appl. No.: 16/496,532

(22) PCT Filed: Mar. 28, 2018

(86) PCT No.: PCT/JP2018/012795
§ 371 (c)(1),
(2) Date: Sep. 23, 2019

(87) PCT Pub. No.: WO2018/181488
PCT Pub. Date: Oct. 4, 2018

(65) Prior Publication Data
US 2021/0278323 A1    Sep. 9, 2021

(30) Foreign Application Priority Data
Mar. 29, 2017    (JP) .................................. 2017-064794

(51) Int. Cl.
*G01N 1/36*    (2006.01)
*B01L 3/00*    (2006.01)
(Continued)

(52) U.S. Cl.
CPC ................ *G01N 1/36* (2013.01); *B01L 3/502* (2013.01); *G01N 21/6428* (2013.01);
(Continued)

(58) Field of Classification Search
CPC ...... G01N 1/36; G01N 21/6428; G01N 21/78; G01N 33/56983; G01N 33/581;
(Continued)

(56) References Cited

U.S. PATENT DOCUMENTS

2003/0070677 A1    4/2003 Handique et al.
2004/0029203 A1    2/2004 Gumbrecht et al.
(Continued)

FOREIGN PATENT DOCUMENTS

CN    102356319 A    2/2012
CN    102859367 A    1/2013
(Continued)

OTHER PUBLICATIONS

International Search Report received for PCT Patent Application No. PCT/JP2018/012795, mailed on Jul. 3, 2018, 4 pages (2 pages of English translation of International Search Report and 2 pages of original International Search Report).
(Continued)

*Primary Examiner* — Dennis White

(57) ABSTRACT

There is provided a method of detecting a microscopic body stored in a plurality of receptacles formed separately from each other. The method, which is provided as a technique for enclosing a to-be-detected substance such as nucleic acid, protein, virus, and cell by means of a simple operation in droplets of an extremely small volume and enabling highly sensitive detection, includes the steps of (1) introducing a solvent into a space between a lower layer part in which the receptacles are formed and an upper layer part facing a surface of the lower layer part in which surface the recep-
(Continued)

tacles are formed, wherein the solvent contains the microscopic body; (2) introducing gas into the space to form a droplet of the solvent in the receptacles, wherein the droplet contains the microscopic body; and (3) detecting the microscopic body present in the droplet optically, electrically, and/or magnetically.

28 Claims, 3 Drawing Sheets

(51) Int. Cl.
    *G01N 21/64* (2006.01)
    *G01N 21/78* (2006.01)
    *G01N 33/569* (2006.01)
    *G01N 33/58* (2006.01)

(52) U.S. Cl.
    CPC ....... *G01N 21/78* (2013.01); *G01N 33/56983* (2013.01); *G01N 33/581* (2013.01); *B01L 2200/142* (2013.01); *B01L 2300/0819* (2013.01); *B01L 2300/0858* (2013.01); *B01L 2300/0864* (2013.01)

(58) Field of Classification Search
    CPC ...... G01N 33/483; G01N 35/08; B01L 3/502; B01L 2200/142; B01L 2300/0819; B01L 2300/0858; B01L 2300/0864; B01L 2200/0605; B01L 2200/0673; B01L 2200/0689; B01L 2400/0406; B01L 3/5027; C12M 1/34; C12Q 1/06; C12Q 1/70
    See application file for complete search history.

(56) References Cited

U.S. PATENT DOCUMENTS

| | | |
|---|---|---|
| 2009/0283148 A1 | 11/2009 | Shinoda et al. |
| 2012/0046187 A1 | 2/2012 | Baba et al. |
| 2012/0070911 A1 | 3/2012 | Peyrade et al. |
| 2012/0111506 A1 | 5/2012 | Rival |
| 2012/0196774 A1 | 8/2012 | Fournier et al. |
| 2013/0043150 A1 | 2/2013 | Ohashi |
| 2013/0345088 A1 | 12/2013 | Noji et al. |
| 2016/0107159 A1* | 4/2016 | Gong ...................... B01L 3/567 435/6.12 |
| 2017/0007998 A1* | 1/2017 | Fraden ...................... C30B 7/00 |
| 2017/0176430 A1* | 6/2017 | Noji ...................... G01N 1/4044 |

FOREIGN PATENT DOCUMENTS

| | | | |
|---|---|---|---|
| JP | 2004-521315 A | 7/2004 | |
| JP | 2004-309405 A | 11/2004 | |
| JP | 2010-054492 A | 3/2010 | |
| JP | 2012-103252 A | 5/2012 | |
| JP | 2012-522237 A | 9/2012 | |
| JP | 2014-503831 A | 2/2014 | |
| WO | 1999/052633 A1 | 10/1999 | |
| WO | 2012/103447 A1 | 8/2012 | |
| WO | 2012/121310 A1 | 9/2012 | |
| WO | WO-2016006208 A1 * | 1/2016 | ............... C12Q 1/04 |
| WO | WO-2016149639 A1 * | 9/2016 | ........ B01L 3/502761 |
| WO | WO-2016161400 A1 * | 10/2016 | ................ B01L 3/00 |

OTHER PUBLICATIONS

European Patent Office, "Extended European Search Report," issued in European Patent Application No. 18 775 227.4, which is an EP counterpart to U.S. Appl. No. 16/496,532, on Apr. 1, 2021, 15 pages.
China National Intellectual Property Administration, "First Office Action", issued in Chinese Patent Application No. 201880021722.1, which is a counterpart to U.S. Appl. No. 16/496,532, on Dec. 26, 2022, 9 pages.

* cited by examiner

MICROSCOPIC BODY DETECTION METHOD AND MICROSCOPIC BODY DETECTION DEVICE

CROSS REFERENCE TO RELATED APPLICATIONS

This patent application is a U.S. national stage application under 35 U.S.C. § 371 of International Patent Application No. PCT/JP2018/012795 filed on Mar. 28, 2018, which claims the benefit of foreign priority to Japanese Patent Application No. JP 2017-064794 filed on Mar. 29, 2017. The International Application was published in Japanese on Oct. 4, 2018, as International Publication No. WO 2018/181488 A1 under PCT Article 21(2).

TECHNICAL FIELD

The present invention relates to a microscopic body detection method and a microscopic body detection device. More specifically, the present invention relates to a method or the like of forming small droplets, in which microscopic bodies are enclosed, in a plurality of receptacles formed separately from each other on a substrate, and detecting the microscopic body present in the droplet optically, electrically, and/or magnetically.

BACKGROUND ART

There has been a need for a technique enabling detection of markers such as nucleic acids, proteins, viruses and cells quickly, in a simplified manner, and with high sensitivity for diagnosis of diseases, infectious diseases, etc. For example, if a marker protein (100 molecules from each cell) is secreted into S liters of blood from one million cancer cells contained in a tumor of 1 $mm^3$ in volume, then the blood concentration of the marker protein is about 30 aM. There has been a need for techniques that enable detection of substances of such very low concentrations.

As one of such techniques, "single molecule enzyme assay" may be mentioned, according to which substances to be detected such as nucleic acids, proteins, viruses, cells, etc. are enclosed in droplets of extremely small volume and detected by an immunological method using a labeled antibody. According to the single molecule enzyme assay, the to-be-detected substances can be detected with the sensitivity at the level of one molecule unit.

Patent Literature 1 discloses, as a technique applicable to single molecule enzyme assay, "a method of sealing beads that includes a beads introduction step of introducing a hydrophilic solvent including beads into a space between a lower layer section including a plurality of receptacles each of which is capable of storing only one of the beads and which are separated from each other by a sidewall having a hydrophobic upper surface and an upper layer section facing a surface of the lower layer section on which surface the plurality of receptacles are provided and a hydrophobic solvent introduction step of introducing a hydrophobic solvent into the space, where the hydrophobic solvent introduction step is carried out after the beads introduction step."

The technique disclosed in Patent Literature 1 uses "an array comprising a lower layer section provided with a plurality of receptacles being separated from each other by a sidewall having a hydrophobic upper surface and an upper layer section facing, via a space, a surface of the lower layer section on which surface the plurality of receptacles are provided," which involves use of an array having a flow cell structure where the lower layer section and the upper layer section face each other via a space. This technique, according to the disclosure, "makes it possible to efficiently seal a large number of beads into an array and thereby detect target molecules of low concentration with high sensitivity."

CITATIONS LIST

Patent Literature

Patent Literature 1: International Publication No. WO 2012/121310
Patent Literature 2: Japanese Patent Laid-Open No. 2004-309405

SUMMARY OF INVENTION

Technical Problem

An object, amongst other objects, of the present invention is to provide a technique for enclosing, to-be-detected substances such as nucleic acids, proteins, viruses, etc. in droplets of an extremely small volume by a simple operation and enabling highly sensitive detection.

Solution to Problem

In order to solve the above-described problem, the present invention provides the following features [1] to [20].
  [1] A method of detecting a microscopic body stored in a plurality of receptacles formed separately from each other, the method including the steps of:
  (1) introducing a solvent into a space between a lower layer part in which the receptacles are formed and an upper layer part facing a surface of the lower layer part in which surface the receptacles are formed, wherein the solvent contains the microscopic body;
  (2) introducing gas into the space to form a droplet of the solvent in the receptacles, wherein the droplet contains the microscopic body; and
  (3) detecting the microscopic body present in the droplet optically, electrically, and/or magnetically.
  [2] A method of optically detecting a microscopic body stored in a plurality of receptacles formed separately from each other, the microscopic body being detected on the basis of a change in absorbance and/or fluorescence of a chromogenic substrate, the method including the steps of:
  (1) introducing a solvent into a space between a lower layer part in which the receptacles are formed and an upper layer part facing a surface of the lower layer part in which surface the receptacles are formed, wherein the solvent contains the microscopic body;
  (2) introducing gas into the space to substitute the solvent in the space by the gas and form a droplet of the solvent in the receptacles, wherein the droplet contains the microscopic body; and
  (3) detecting the change in absorbance and/or the fluorescence of the chromogenic substrate present in the droplet.
  [3] The method according to the item [1] or [2], further including means for suppressing transpiration of the droplet.
  [4] The method according to the item [3], wherein an aspect ratio of each of the receptacles is equal to or larger than 1.

[5] The method according to the item [3], further including, prior to the step (2), a step of bringing the gas into contact with water.
[6] The method according to the item [3], wherein a reservoir is formed in the lower layer part such that the solvent is allowed to be held in the reservoir, the reservoir having an internal volume larger than an internal volume of each of the receptacles.
[7] The method according to the item [3], wherein the steps (2) and (3) are performed in a humid environment.
[8] The method according to the item [3], wherein the solvent contains a highly hydratable substance.
[9] A substance detection device that includes:
  a substrate that includes a lower layer part in which a plurality of receptacles are formed and an upper layer part facing a surface of the lower layer part in which surface the receptacles are formed, wherein a microscopic body is allowed to be stored in the receptacles, the receptacles being formed separately from each other;
  a liquid feeding unit that introduces a solvent into a space between the lower layer part and the upper layer part of the substrate;
  an air feeding unit that introduces gas into the space; and
a detector that detects the microscopic body present in the receptacles optically, electrically, and/or magnetically.
[10] The device according to the item [9], further including means for suppressing transpiration of the droplet.
[11] The device according to the item [10], wherein an aspect ratio of each of the receptacles is equal to or larger than 1.
[12] The device according to the item [10], wherein the air feeding unit includes a tank in which the gas is brought into contact with water.
[13] The device according to any one of the item [10], wherein the substrate includes a reservoir in the lower layer part such that the solvent is allowed to be held in the reservoir, the reservoir having an internal volume larger than an internal volume of each of the receptacles.
[14] The device according to the item [10], further including a chamber that maintains the substrate in a humid environment.
[15] A substance detection device to which a substrate can be mounted, the substrate including a lower layer part in which a plurality of receptacles are formed and an upper layer part facing a surface of the lower layer part in which surface the receptacles are formed, wherein a microscopic body is allowed to be stored in the receptacles and the receptacles are formed separately from each other, the substance detection device comprising:
  a liquid feeding unit that introduces a solvent into a space between the lower layer part and the upper layer part of the substrate;
  an air feeding unit that introduces gas into the space; and
  a detector that detects the microscopic body present in the receptacles optically, electrically, and/or magnetically.
[16] The device according to the item [15], further including means for suppressing transpiration of the droplet.
[17] The device according to the item [16], wherein an aspect ratio of each of the receptacles is equal to or larger than 1.
[18] The device according to the item [16], wherein the air feeding unit includes a tank in which the gas is brought into contact with water.
[19] The device according to the item [16], wherein the substrate includes a reservoir in the lower layer part such that the solvent is allowed to be held in the reservoir, the reservoir having an internal volume larger than an internal volume of each of the receptacles.
[20] The device according to the item [16], further comprising a chamber that maintains the substrate in a humid environment.

Advantageous Effects of Invention

The present invention provides a technique for enclosing to-be-detected substances such as nucleic acids, proteins, viruses, etc. in droplets of an extremely small volume by a simplified operation and enabling highly sensitive detection.

BRIEF DESCRIPTION OF DRAWINGS

FIG. 1-2 is a diagram explaining a step of a substance detection method in accordance with the present invention.
FIG. 2 is a diagram for explanation of a reaction product resulting from the reaction between an enzyme present on a surface of a virus particle and a chromogenic substrate.

DESCRIPTION OF EMBODIMENTS

Figure 1:
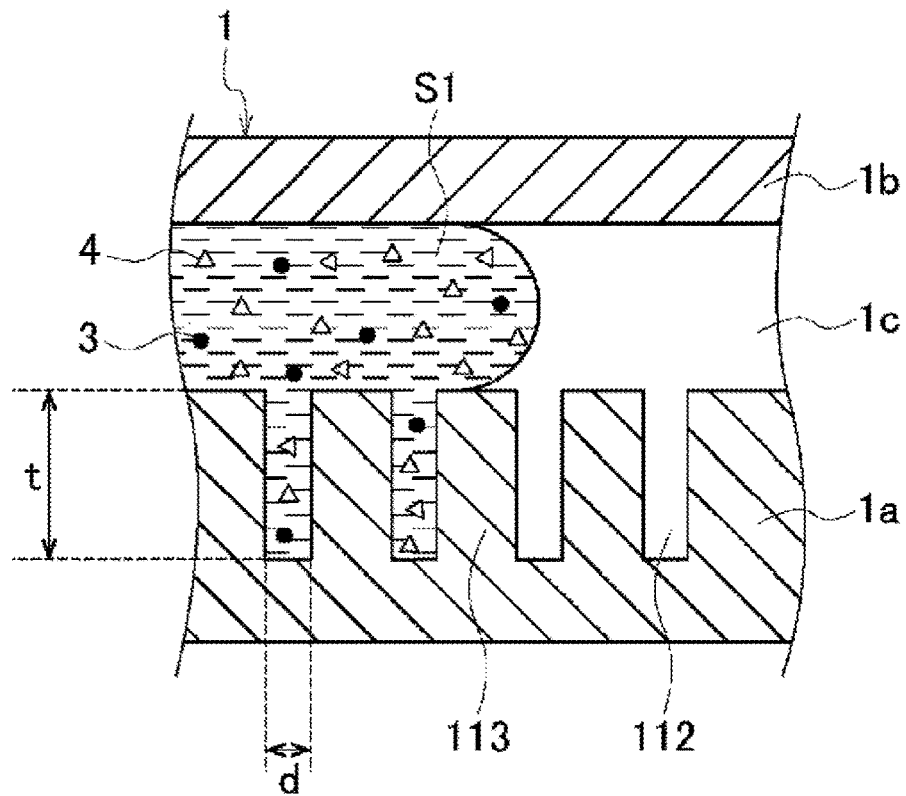
FIG. 1-1 is a diagram explaining a step of a substance detection method in accordance with the present invention.
Figure 1:
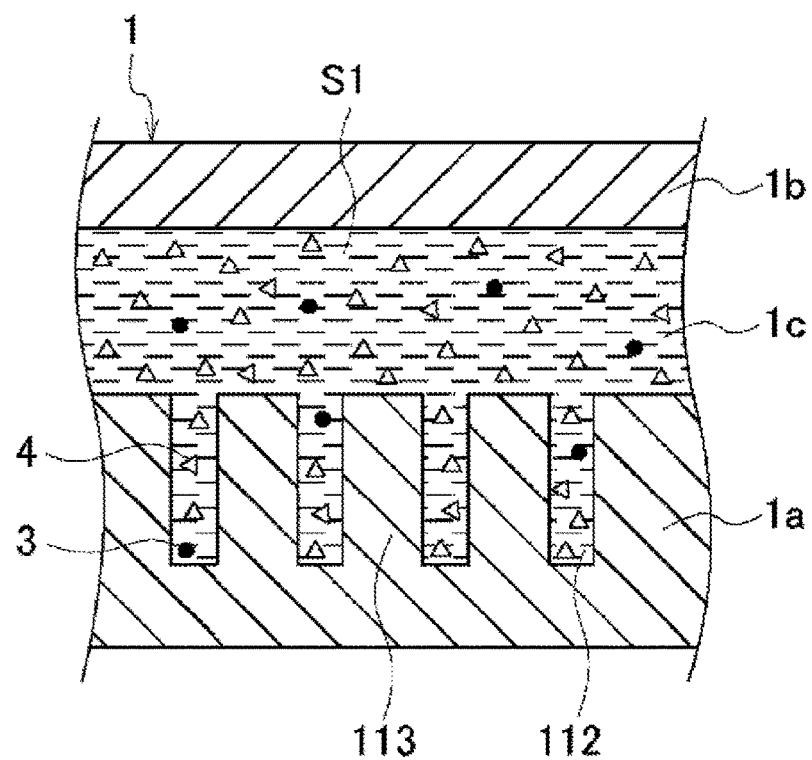
Figure 1:
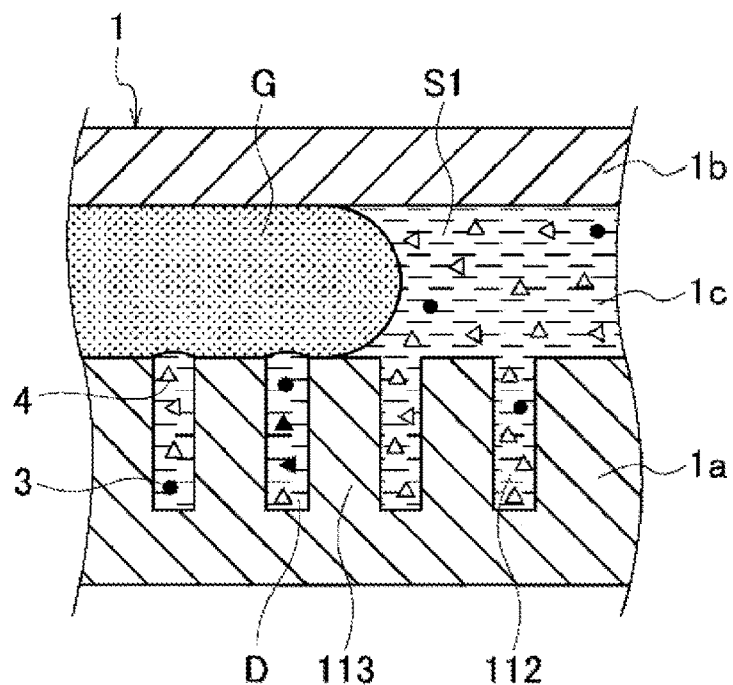

Preferable embodiments of the present invention will be described hereinbelow with reference to the drawings. It should be noted that the embodiments described hereinbelow depict an example of a representative embodiment of the present invention, by which the scope of the present invention is in no way interpreted in a limitative manner.

The substance detection method in accordance with the present invention includes the following steps (A), (B), and (C):
  (A) The step of introducing a solvent into a space between a lower layer part of an array in which the receptacles are formed and an upper layer part of the array facing a surface of the lower layer part in which surface the receptacles are formed, wherein the solvent contains the microscopic body (substance introduction step).
  (B) The step of introducing gas into the space to substitute the solvent in the space by the gas and form a droplet of the solvent in the receptacles, wherein the droplet contains the microscopic body (substance storage step).
  (C) The step of detecting the microscopic body present in the droplet optically, electrically, and/or magnetically (detection step).

The specific steps of the substance detection method in accordance with the present invention will be described hereinbelow.

[Substance to be Detected]

The microscopic body that should be detected by the substance detection method or the like in accordance with the present invention (which may also be hereinafter referred to as a "target substance") is not limited to a particular one as long as the microscopic body is a substance with a size that allows the substance to be accommodated in the receptacle. Target substance may be a nucleic acid, a protein, a sugar, a lipid, and a complex thereof, as well as a virus. The target substance is preferably a nucleic acid, a protein, a sugar, a lipid, and a complex thereof, which can be a marker of various diseases or infectious diseases.

Nucleic acids include natural nucleic acids such as DNA and RNA, and artificial nucleic acids such as LNA and PNA, and also include polymers thereof.

The target substance may be held by a carrier. Microbeads are widely used as such a carrier. Here, the term "microbead" is used synonymously with "particle." Microbeads pertain to commonly used techniques in the technical field. Although the shape of the microbead is not limited to a particular one, the shape of the microbead is usually spherical. The material of the microbeads is not limited to any particular one, either, and may be glass, silica gel, polystyrene, polypropylene, membrane, magnetic material, etc. As specific materials, cellulose, cellulose derivative, acrylic resin, glass, silica gel, polystyrene, gelatin, polyvinyl pyrrolidone, copolymer of vinyl and acrylamide, polystyrene crosslinked with divinylbenzene or the like, polyacrylamide, latex gel, polystyrene dextran, rubber, silicon, plastic, nitrocellulose, cellulose, natural sponge, silica gel, glass, metal plastic, cellulose, cross-linked dextran (Sephadex™), and agarose gel (Sepharose™) may be mentioned. The beads may be porous. The beads preferably have an average particle diameter of 5 μm or less, and for example, about 1 μm to 4 μm. It should be noted that the average particle diameter can be measured using electron microscope observation or dynamic light scattering, for example.

[Array]

The array 1 of the device used in the substance detection method in accordance with the present invention (see FIG. 1(A)) includes a lower layer part 1a in which a plurality of receptacles 112 for storing a target substance are formed and an upper layer part 1b facing the lower layer part 1a. The lower layer part 1a and the upper layer part 1b face each other with a space 1c residing in between. The respective receptacles 112 are separated from each other by sidewalls 113. The receptacles 112 each have an opening continuing to the space 1c between one sidewall 113 and another sidewall 113. Numerous receptacles 112 are arranged in the direction parallel to the surface of the lower layer part 1a of the array 1 and target substances can be captured into the receptacles 112 via their openings.

The array 1 can be formed using known techniques such as wet etching or dry etching of a glass substrate layer, or nanoimprinting, injection molding, or cutting of a plastic substrate layer. The material of the array 1 is a material having optical transparency in the case of optical detection of a target substance, and may be glass or various plastics (PP, PC, PS, COC, COP, PDMS, etc.). As the material of the array 1, it is preferable to select a material that causes less optical errors due to having less autofluorescence and less wavelength dispersion.

The distance between the surfaces of the lower layer part 1a and the upper layer part 1b facing each other (the height of the space 1c) is not subject to particular limitations but is about 10 μm to 100 μm.

The size (volume) and shape of the receptacles 112 are defined such that the target substance can be stored in the receptacle 112. If the target substance is any of a nucleic acid, a protein, a sugar, a lipid, and a complex thereof; or a virus, then the size of the receptacles 112 is, for example, about 0.1 μm to 10 μm in diameter at their bottom, with its height (depth) being about 0.1 μm to 10 μm where their volume will be about 1 zeptolitre to 1 attolitre. The shape of the receptacle 112 is preferably cylindrical or prismatic considering ease of formation of the receptacle 112.

Further, for creation of droplets in the substance storage step which will be described later, the aspect ratio of the receptacle 112 is 1 or more; preferably 1.1 or more, 1.2 or more, 1.3 or more, 1.4 or more; more preferably 1.5 or more, 1.6 or more, 1.7 or more, 1.8 or more, 1.9 or more; or further more preferably 2.0 or more, 2.1 or more, 2.2 or more, 2.3 or more, 2.4 or more, or a value greater than 2.5.

Also, the aspect ratio can be set to 1 to 2.5, preferably 1.5 to 2.5, and more preferably 2.0 to 2.5.

The aspect ratio is a ratio defined as t/d, where d is the diameter of the bottom surface of the receptacle 112 (which is identical with the diameter of the opening if the receptacle 112 is a cylinder or a cuboid) and t is the height of the receptacle 112. Here, if the bottom surface of the receptacle 112 is elliptical, rectangular, etc., then the diameter d should refer to the diameter in the longitudinal direction of the bottom surface. And the depth t should refer to the maximum depth of the receptacle 112.

[Substance Introduction Step]

First, a first solvent S1 that contains the target substance 3 is introduced into the space 1c (see FIG. 1(A)).

Here, an example will be described in which a chromogenic substrate 4 for optically detecting the target substance 3 based on the change in absorbance and/or the fluorescence is introduced together with the target substance 3.

The first solvent S1 may be any solvent suitable for dissolving or suspending the target substance 3 and the chromogenic substrate 4, and a solvent that is usually used when detecting nucleic acids, proteins, sugars, lipids, and complexes thereof, as well as viruses, etc. is used as the first solvent. The first solvent S1 may contain, for example, at least one selected from the group consisting of water, alcohol, ether, ketone, nitrile solvent, dimethyl sulfoxide (DMSO), and N,N-dimethylformamide (DMF), or a mixture including the selected one, among which water is preferable. Examples of the alcohol may include ethanol, methanol, propanol, glycerin, and the like. Examples of the ether may include tetrahydrofuran, polyethylene oxide, 1,4-dioxane, and the like. Examples of the ketone may include acetone, methyl ethyl ketone, and the like. Examples of the nitrile solvent may include acetonitrile and the like.

The first solvent S1 may contain a buffer substance. While the buffer substance is not limited to a particular one, so-called Good's Buffers such as MES (2-morpholinoethanesulfonic acid), ADA (N-(2-acetamido) iminodiacetic acid), PIPES (piperazine-1,4-bis (2-ethanesulfonic acid)), ACES (N-(2-Acetamido)-2-aminoethanesulfonic acid), BES (N,N-Bis(2-hydroxyethyl)-2-aminoethanesulfonic acid), TES (N-Tris(hydroxymethyl)methyl-2-aminoethanesulfonic acid), HEPES (4-(2-hydroxyethyl)-1-piperazineethanesulfonic acid); Tris (Tris(hydroxymethyl)aminomethane); DEA (Diethanolamine); and the like may be used according to the pKa of the fluorescent dye.

Also, the first solvent may contain a surfactant. When the first solvent contains the surfactant, the first solution S1 can be more easily introduced into the space 1c and the receptacle 112. While the surfactant is not subject to particular limitations, for example, TWEEN 20 (CAS number: 9005-64-5, polyoxyethylene sorbitan monolaurate) and Triton X-100 (CAS number: 9002-93-1 with the generic name of polyethylene glycol mono-4-octylphenyl ether (where n≈10)) may be mentioned. The concentration of the surfactant added to the first solvent S1 is not subject to particular limitations but is preferably 0.01 to 1%.

Further, as the surfactant, anionic surfactants, cationic surfactants, nonionic surfactants, amphoteric surfactants, surfactants of natural origin, and the like can be widely used.

Anionic surfactants are classified into, for example, a carboxylic acid type, a sulfuric acid ester type, a sulfonic acid type, and a phosphoric acid ester type. Among these types, specifically, for example, sodium dodecyl sulfate, sodium laurate, sodium α-sulfofatty acid methyl ester, sodium dodecyl benzene sulfonate, sodium dodecyl ethoxylate sulfate, and the like may be mentioned, amongst which sodium dodecyl benzene sulfonate is preferably used.

Cationic surfactants are classified into, for example, a quaternary ammonium salt type, an alkylamine type, and a heterocyclic amine type. Specifically, for example, stearyl trimethyl ammonium chloride, distearyl dimethyl ammonium chloride, didecyl dimethyl ammonium chloride, cetyl tripyridinium chloride, dodecyl dimethyl benzyl ammonium chloride, and the like may be mentioned.

As the nonionic surfactant, for example, polyoxyethylene alkyl ether, polyoxyethylene hydrogenated castor oil, polyoxyethylene mono-fatty acid ester, polyoxyethylene sorbitan mono-fatty acid ester, sucrose fatty acid ester, polyglycerin fatty acid ester, alkyl polyglycoside, N-methyl alkyl glucamide, and the like may be mentioned. Amongst others, in addition to dodecyl alcohol ethoxylate, nonylphenol ethoxylate, lauroyl diethanolamide, those sold with the names of Triton X (such as Triton X-100), Pluronic (registered trademark) (such as Pluronic F-123, F-68), Tween (such as Tween 20, 40, 60, 65, 80, 85), Brij (registered trademark) (such as Brij 35, 58, 98), Span (Span 20, 40, 60, 80, 83, 85) will be preferable.

As the amphoteric surfactants, for example, lauryl dimethylaminoacetic acid betaine, dodecylaminomethyldimethylsulfopropylbetaine, 3-(tetradecyldimethylaminio)propane-1-sulfonate, are available, but it is preferable to use 3-[(3-cholamidopropyl)dimethylammonio]-1-propane-sulfonate (CHAPS), 3-[(3-cholamidopropyl)dimethylammonio]-2-hydroxy-1-propanesulfonate (CHAPSO), or the like.

As a surfactant of natural origin, for example, lecithin and saponin are preferable, and among compounds referred to as lecithin, specifically, phosphatidylcholine, phosphatidylethanolamine, phosphatidylinositol, phosphatidylserine, phosphatidic acid, phosphatidylglycerol, and the like are preferable. Also, quillaja saponin is preferable as the saponin.

The first solvent S1 that contains the target substance 3 and the chromogenic substrate 4 should be injected, for example, via an inlet provided in the upper layer part 1b and connected to the space 1c. It should be noted that an outlet through which the solvent and gas are discharged can be connected to the opposite side of the inlet connection side of the space 1c. The first solvent S1 that has been introduced into the space 1c flows in the space between the lower layer part 1a and the upper layer part 1b through capillary action and the space 1c is filled with the first solvent S1 (see FIG. 1(B)). As a result, the target substance 3 and the chromogenic substrate 4 are introduced into the receptacle 112.

If the concentration of the target substance 3 in the first solvent S1 is low, one molecule of the target substance 3 is introduced into each receptacle 112 or not introduced at all. Also, if the concentration of the target substance 3 in the first solvent S1 is higher, two or more target substances 3 can be introduced into each receptacle 112.

Meanwhile, it is preferable that the chromogenic substrate 4 be contained in the first solvent S1 at a sufficiently high concentration as compared to the concentration of the target substance 3. Accordingly, one molecule or two or more molecules of the chromogenic substrate 4 will be introduced into almost all of the receptacles 112.

The substance detection device in accordance with the present invention may include, in addition to the array 1 a liquid feeding unit that introduces the first solvent S1 into the space 1c. The liquid feeding unit includes a tank into which the first solvent S1 is supplied, a tube interconnecting the tank and the above-described inlet, a pump, etc.

The substance detection device in accordance with the present invention may include a temperature controller in addition to the array 1 and the above-described liquid feeding unit. The temperature controller may be a heat block capable of temperature control of the array 1 through a Peltier element, a Joule-Thomson element, or the like.

[Substance Storage Step]

Next, gas G is introduced into the space 1c (see FIG. 1(C)). The gas G may be injected via the same inlet as that via which the first solvent S1 is introduced or via another inlet different than that, and may be discharged via the same outlet as that via which the first solvent S1 is discharged or via another outlet different than that. The substance detection device in accordance with the present invention may include, in addition to the array 1 and the above-described liquid feeding unit, an air feeding unit that introduces the gas G into the space 1c. The air feeding unit includes a tank into which the gas G is supplied, a tube interconnecting the tank and the above-described inlet, a pump, etc.

While the gas G is not limited to a particular one as long as it is gaseous at an ambient temperature in this step (which may be, and is not limited to, a room temperature), for example, air or nitrogen gas can be suitably used.

The gas G that has been introduced into the space 1c replaces the first solvent S1 with which the space 1c has been filled and proceeds in the space 1c. As a result, a droplet D of the first solvent S1 containing the chromogenic substrate 4 is formed in the receptacle 112 (see FIG. 1(C)). The target substance 3 is enclosed along with the chromogenic substrate 4 into the droplets D of a predetermined percentage formed in the receptacles 112.

It should be noted that the introduction of the gas G may be carried out by a method according to which the gas G is injected via the inlet or another method according to which the gas G is introduced via the inlet by applying negative pressure from the outlet. At this point, air may be introduced via the inlet by applying negative pressure to the outlet in a state where the inlet is open. Further, the first solvent S1 with which the space 1c has been filled may be discharged via the outlet and the air may be introduced via the inlet by applying to the array 1 a centrifugal force in the direction from the inlet to the outlet in a state where the inlet is open. As such a method of applying centrifugal force, a method may be mentioned according to which the array 1 is placed upon a rotating plate.

In this step, in order to ensure that the solvent S1 is readily held in the receptacle 112 to promote formation of the droplets D or to suppress transpiration of the droplets D, the aspect ratio of the receptacle 112 is set to 1 or more; preferably 1.1 or more, 1.2 or more, 1.3 or more, or 1.4 or more; more preferably 1.5 or more, 1.6 or more, 1.7 or more, 1.8 or more, or 1.9 or more; further more preferably 2.0 or more, 2.1 or more, 2.2 or more, 2.3 or more, 2.4 or more, or a value greater than 2.5.

Also, the aspect ratio can be set to 1 to 2.5, preferably 1.5 to 2.5, or more preferably 2.0 to 2.5.

If the aspect ratio is so small that it is out of this range, then, in some cases, the first solvent S1 in the receptacle 112 may be accidentally substituted by the gas G and the droplets D may be lost because of transpiration, as a result of which the efficiency in the formation of the droplets D may decrease. It should be noted that the first solvent S1 can be more easily held in the receptacle 112 by increasing the depth of the receptacle 112 relative to the diameter of the opening continuing to the space 1c.

In order to promote formation of the droplets D or suppress the transpiration of the droplets D so as to maintain the formation of the droplets D, it is preferable to perform a step of bringing the gas G into contact with water prior to this step. When the gas G is brought into contact with water and the water vapor saturation of the gas G introduced into the space 1c is increased in advance, it is made possible to suppress evaporation of the first solvent S1 held in the receptacle 112 and promote the formation of the droplets D and suppress transpiration of the droplets D.

Dry air may promote evaporation of the solvent and saturated air may cause instability in the operation. In view of this, if the moisture contained in the gas is defined by relative humidity, then the relative humidity is preferably about 50 to 80% in the present invention, provided that a predetermined operation is performed at about normal temperature.

The air feeding unit of the substance detection device in accordance with the present invention preferably includes a tank in which the gas G is brought into contact with water.

Also, in order to suppress evaporation of the first solvent S1 held in the receptacles 112 and transpiration of the droplets D, it is also preferable to maintain the water vapor saturation of the space 1c at a high level. For this purpose, it may be effective to provide a reservoir in the lower layer part 1a so that the first solvent S1 can be held in the reservoir, where the internal volume of the reservoir is made larger than the internal volume of the receptacle 112. When the reservoir is provided, the first solvent S1 that has been introduced into the reservoir in the substance introduction step is allowed to serve as a water supply source (liquid pool) for increasing the water vapor saturation of the space 1c in this step. One reservoir or two or more reservoirs can be provided in the lower layer part 1a at a location which does not affect the detection of the target substance 3.

Further, in order to suppress evaporation of the first solvent S1 held in the receptacles 112 and transpiration of the droplets D, it may also be effective to perform this step and the subsequent detection step in a humid environment. For this purpose, the substance detection device in accordance with the present invention preferably includes a chamber for maintaining the array 1 in its inside to keep the array 1 in a humid environment.

In the case where the first solvent S1 is water, a highly hydratable substance may be added to the first solvent S1 in order to suppress evaporation of the first solvent S1 held in the receptacle 112 and transpiration of the droplets D. As the highly hydratable substance retains water, evaporation of the first solvent S1 can be suppressed.

The highly hydratable substance is not subject to particular limitations as long as the highly hydratable substance does not affect the optical, electrical, and/or magnetic detection of the target substance 3 in the detection step which will be described later. For example, gels of agarose, acrylamide; etc.; hydrophilic polymers of polyethylene glycol, cellulose, etc.; and osmolytes such as glycine, betaine, sorbitol, sucrose, mannitol, trehalose, urea, etc. can be suitably used. The addition concentration of these highly hydratable substances to the first solvent S1 is, for example, about 0.1 to 5%, preferably about 0.5 to 2%.

In the next detection step, the target substance 3 present in the droplet D is detected optically, electrically, and/or magnetically. In the example described herein, the target substance 3 is optically detected through detection of the change in absorbance and/or fluorescence of the chromogenic substrate 4. More specifically, the explanation will be provided based, by way of example, on a case where the target substance 3 is a virus having on its surface or in its inside an enzyme having substrate cleaving activity vis-a-vis the chromogenic substrate 4 and the chromogenic substrate 4 is a substance which is cleaved by the enzyme to release a reaction product as a chromophore. However, while the chromogenic substrate 4 should be able to form a reaction product having optical characteristics after the reaction different from those before the reaction with the enzyme, the chromogenic substrate 4 may be a substance whose absorbance or optical rotation changes before and after the reaction, or a substance that exhibits fluorescence after the reaction.

Examples of combinations of such a virus and such an enzyme may be as follows.

TABLE 1

| | |
|---|---|
| Coronavirus | Hemagglutinin esterase |
| SARS virus | Hemagglutinin esterase |
| MARS virus | Hemagglutinin esterase |
| Influenza virus | Neuraminidase |
| Mumps virus (epidemic parotiditis) | Neuraminidase |
| Measles virus | Neuraminidase |
| Nipah virus | Neuraminidase |
| Canine distemper virus | Neuraminidase |

Figure 2:
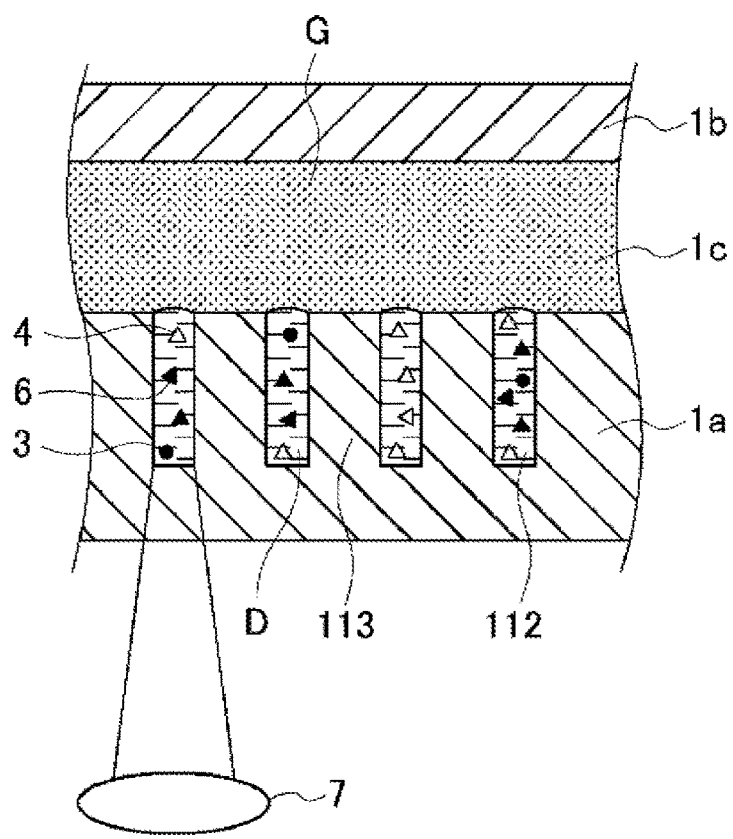
Figure 2:
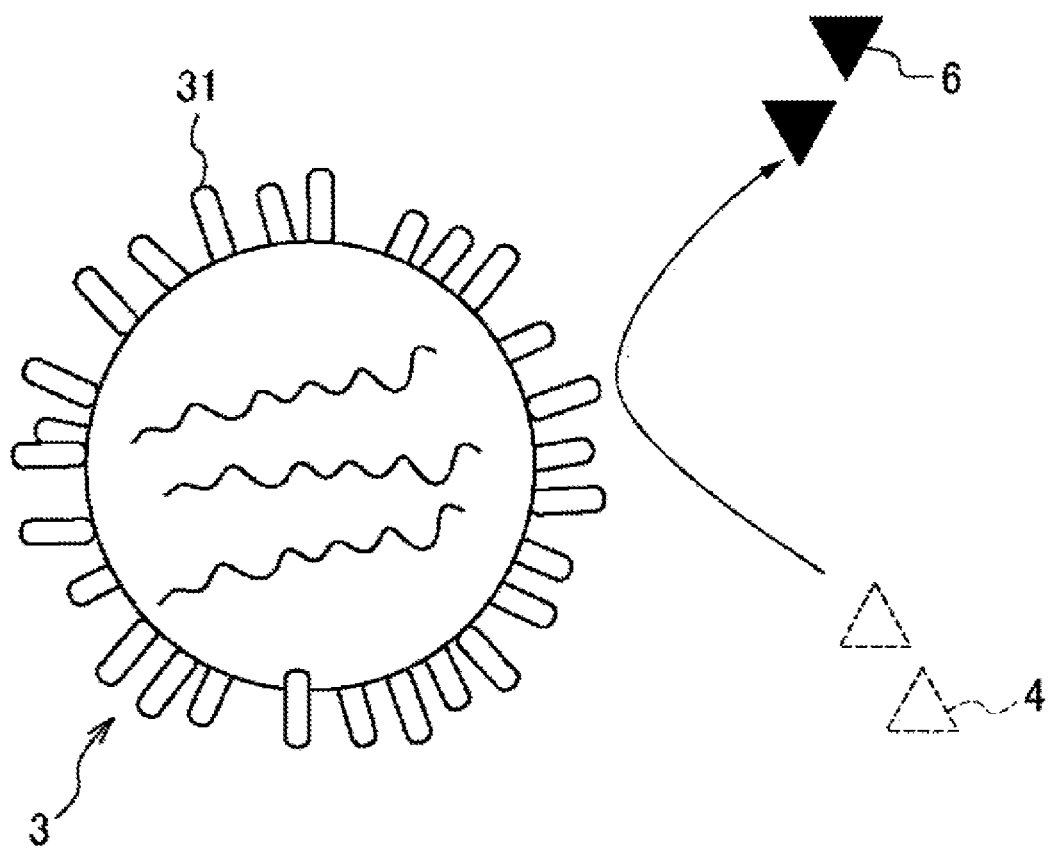

In the droplet D formed in the receptacle 112, the reaction proceeds between the enzyme present on the surface of or in the inside of the target substance 3 (virus particle) and the chromogenic substrate 4, which coexist in the minimal volume, as a result of which a reaction product is formed. This will be described in detail with reference to FIG. 2. The enzyme 31 is present on the surface of or in the inside of the virus particle (in the illustrated case, the enzyme 31 is present on the virus surface). When the chromogenic substrate 4 contacts and reacts with the enzyme 31, a reaction product 6 is formed. The reaction product 6 exhibits optical characteristics different than those of the chromogenic substrate 4, and exhibits a shift in the absorbance or optical rotation or exhibits fluorescence (or luminescence).

Reaction of the enzyme 31 with the chromogenic substrate 4 forms and accumulates the reaction product 6 in a minimal volume (in the order of zeptolitres to attolitres) of the droplet D. Further, since the droplet D is not in interfacial contact with other solvents or solutions, the reaction product 6 formed and accumulated in the droplet D does not leak from the droplet D. These enable rapid creation of the reaction product 6 to a detectable concentration in the next detection step, thus enabling highly sensitive detection of the reaction product 6 in the detection step.

More specific explanations will be provided, by way of example, based on a case where the virus is an influenza virus (see Table 1) and 4-methylumbelliferyl-α-D-neuraminic acid (4-methylumbelliferyl-N-acetyl-α-D-neuraminic acid: 4MU-NANA) is used as the chromogenic substrate 4.

Neuraminidase (enzyme 31) is present on the particle surface of the influenza virus. When the 4MU-NANA (chromogenic substrate 4) contacts and reacts with the neuraminidase, 4-methyl umbelliferone (reaction product 6) is formed as a chromophore which exhibits fluorescence derived from hydrolysis of the 4MU-NANA by the neuraminidase. The 4-methyl umbelliferone is accumulated in the minimal volume of the droplet D, and the accumulated 4-methyl umbelliferone exhibits enhanced fluorescence.

While the reaction product 6 may be a product that can be formed when the chromogenic substrate 4 and the enzyme 31 contact each other in the first solvent S1 prior to this step, the reaction product 6 is not accumulated in the minimal volume before the droplet D of the first solvent S1 including the target substance 3 and the chromogenic substrate 4 is formed in this step. As a result, for this reason, in the detection of the reaction product 6, the influence of the reaction product 6 formed prior to this step is negligibly small.

[Detection Step]

In this step, the target substance 3 present in the droplet D is detected optically, electrically, and/or magnetically (see FIG. 1(D)). In the specific example described herein, the influenza virus as the target substance 3 is detected by detecting the fluorescence exhibited by the reaction product 6 (4-methylumbelliferone) formed in the droplet D.

Optical detection can be carried out by a detector 7 that includes a light source, an optical path for collecting light from the light source in the inside of the receptacle 112 and collecting the resulting light from the inside of the receptacle 112 onto a sensor, and the sensor. The substance detection device in accordance with the present invention may include a detector 7 in addition to the array 1, the above-described liquid feeding unit, and the above-described air feeding unit. The light emitted from the light source travels via the lower side of the array 1 (opposite to the opening surface of the receptacle 112) into the receptacle 112, and the resulting light from the inside of the receptacle 112 is also collected via the same side. Lenses, filters, etc. used usually are arranged between the light source and the array 1 and between the array 1 and the sensor such as a CMOS image sensor.

Also, the microscopic body detection device in accordance with the present invention may include a temperature controller that controls the temperature of the array 1. The heating mechanism or temperature control mechanism disclosed in Patent Literature 2 can be adopted as the temperature controller. The temperature controller may be a heat block capable of temperature control, for example, by a Peltier element, a Joule-Thomson element, or the like.

As described above, the reaction product 6 can be formed in the first solvent S1 even before the substance storage step. Meanwhile, many of the reaction products 6 generated before the substance storage step are removed to the outside as the first solvent S1 is substituted by the gas G in the substance storage step. For this reason, in the detection of the reaction product 6 in this step, the reaction product 6 formed before the substance storage step does not act as noise, and the signal from the reaction product 6 formed and accumulated in the minimal volume of the droplet D can be selectively detected.

When the concentration of the target substance 3 in the first solvent S1 is relatively high in the substance introduction step, two or more target substances 3 can be introduced into each of the droplet D. In this case, the fluorescence of the 4-methyl umbelliferone (reaction product 6) in the droplet D is detected, and the enzyme activity of the neuraminidase is calculated using the acquired fluorescence intensity and a standard curve defining the relationship between the fluorescence intensity and neuraminidase activity prepared in advance. Further, determination of the presence or absence of the influenza virus or quantification of the number of particles (analog quantification) is carried out using the calculated enzyme activity and a standard curve defining the relationship between the enzyme activity and the number of virus particles prepared in advance. Thus, the influenza virus as target substance 3 can be detected and the amount of viruses can also be determined quantitatively.

On the other hand, when the target substance 3 is diluted to a sufficiently low concentration in the first solvent S1, the number of target substances 3 entering one receptacle 112 may be 0 or at most 1. In this case, the concentration of the target substance 3 can also be determined by using the ratio between the number of the receptacles 112 at which the target substances 3 have been detected and the number of the receptacles 112 at which the target substance 3 has not been detected and on the basis of a standard curve created in advance and defining the relationship between the concentration of the target substance 3 in the first solvent S1 and the aforementioned ratio (digital quantification).

In the substance storage step, the reaction product 6 can be accumulated at a high concentration in the droplet D of the first solvent S1. As a result, even when only one particle of virus as the target substance 3 is in the receptacle 112, the reaction product 6 can be detected with high sensitivity. Accordingly, according to the substance detection method in accordance with the present invention, even a very small amount of the target substance 3 such as a virus can be detected with high sensitivity, and the amount thereof can be determined with high precision.

According to this embodiment, it is possible to achieve a large-area array 1 having a large number of receptacles 112. For example, even in case of an array 1 having one million or more receptacles 112, the target substance 3 can be efficiently stored in each of the receptacles 112. Accordingly, since this embodiment enables detection of the target substance 3 with high sensitivity, it is made possible to detect the target substance 3 with a very low concentration in the order of 10 aM, which can be applied, for example, to applications such as Digital ELISA, ELISA-PCR, etc.

REFERENCE SIGNS LIST

1: array; 1a: lower layer part; 1b: upper layer part; 1c: space; 112: receptacle; 113: sidewall; 3: target substance; 4: chromogenic substrate; 6: reaction product; 7: detector; D: droplet; G: gas; S1: first solvent

The invention claimed is:

1. A method of detecting a microscopic body stored in a plurality of receptacles formed separately from each other, the method comprising the steps of:
(1) providing a substrate that includes
a lower layer part in which the plurality of receptacles for storing the microscopic body and sidewalls separating the respective receptacles from each other are formed,
an upper layer part facing the lower layer part, and
a space across which the lower layer part and the upper layer part face each other, the space residing in between the lower layer part and the upper layer part,
wherein the receptacles each have a cavity and an opening between one sidewall and another sidewall and are connected to the space;
(2) introducing a hydrophilic solvent containing the microscopic body into the space and thereby the hydrophilic solvent containing the microscopic body being further introduced into each of the receptacles via the opening to fill up the cavity of the receptacles;

(3) introducing gas into the space to substitute the hydrophilic solvent containing the microscopic body in the space by the gas and thereby disconnect fluid connection via the space between the receptacles leaving the hydrophilic solvent containing the microscopic body filled up in the cavity of the receptacles; and (4) detecting the microscopic body present in the receptacles optically, electrically, and/or magnetically;

wherein transpiration of the hydrophilic solvent that fills up the cavity of the receptacles is suppressed by a hydratable substance contained in the hydrophilic solvent, wherein the hydratable substance is a gel, a hydrophilic polymer, or an osmolyte.

2. The method according to claim 1, wherein the distance between the lower layer part and the upper layer part is about 10 μm to 100 μm.

3. The method according to claim 1, wherein:
the receptacles each have only one opening; and
the opening has the same diameter as the diameter d of the bottom surface of the receptacle.

4. The method according to claim 1, wherein in the step (2), the hydrophilic solvent flows in the space through capillary action.

5. The method according to claim 1, wherein the hydrophilic solvent containing the microscopic body is homogeneous.

6. The method according to claim 1, wherein:
the gel is selected from the group consisting of agarose and acrylamide;
the hydrophilic polymer is selected from the group consisting of polyethylene glycol and cellulose; and
the osmolyte is selected from the group consisting of glycine, betaine, sorbitol, sucrose, mannitol, trehalose, and urea.

7. The method according to claim 6, wherein the hydratable substance is contained in the hydrophilic solvent at a concentration of about 0.1 to 5%.

8. The method according to claim 1, wherein the hydratable substance is the gel or the hydrophilic polymer.

9. A method of optically detecting a microscopic body stored in a plurality of receptacles formed separately from each other, the microscopic body being detected on the basis of a change in absorbance and/or fluorescence of a chromogenic substrate, the method comprising the steps of:

(1) providing a substrate that includes
a lower layer part in which the plurality of receptacles for storing the microscopic body and sidewalls separating the respective receptacles from each other are formed,
an upper layer part facing the lower layer part, and
a space across which the lower layer part and the upper layer part face each other, the space residing in between the lower layer part and the upper layer part,
wherein the receptacles each have a cavity and an opening between one sidewall and another sidewall and are connected to the space;

(2) introducing a hydrophilic solvent containing the microscopic body into the space and thereby the hydrophilic solvent containing the microscopic body being further introduced into each of the receptacles via the opening to fill up the cavity of the receptacles;

(3) introducing gas into the space to substitute the hydrophilic solvent containing the microscopic body in the space by the gas and thereby disconnect fluid connection via the space between the receptacles leaving the hydrophilic solvent containing the microscopic body filled up in the cavity of the receptacles; and (4) detecting the change in absorbance and/or the fluorescence of the chromogenic substrate present in the receptacles;

wherein transpiration of the hydrophilic solvent that fills up the cavity of the receptacles is suppressed by a hydratable substance contained in the hydrophilic solvent, wherein the hydratable substance is a gel, a hydrophilic polymer, or an osmolyte.

10. The method according to claim 9, wherein the distance between the lower layer part and the upper layer part is about 10 μm to 100 μm.

11. The method according to claim 9, wherein:
the receptacles each have only one opening; and
the opening has the same diameter as the diameter d of the bottom surface of the receptacle.

12. The method according to claim 9, wherein in the step (2), the hydrophilic solvent flows in the space through capillary action.

13. The method according to claim 9, wherein the hydrophilic solvent containing the microscopic body is homogenous.

14. The method according to claim 9, wherein:
the gel is selected from the group consisting of agarose and acrylamide;
the hydrophilic polymer is selected from the group consisting of polyethylene glycol and cellulose; and
the osmolyte is selected from the group consisting of glycine, betaine, sorbitol, sucrose, mannitol, trehalose, and urea.

15. The method according to claim 14, wherein the hydratable substance is contained in the hydrophilic solvent at a concentration of about 0.1 to 5%.

16. The method according to claim 9, wherein the hydratable substance is the gel or the hydrophilic polymer.

17. A substance detection device comprising:
a substrate that includes
a lower layer part in which a plurality of receptacles for storing a microscopic body and sidewalls separating the respective receptacles from each other are formed,
an upper layer part facing the lower layer part, and
a space across which the lower layer part and the upper layer part face each other, the space residing in between the lower layer part and the upper layer part,
wherein the receptacles each have a cavity and an opening between one sidewall and another sidewall and are connected to the space;
a liquid feeding unit that introduces a hydrophilic solvent containing the microscopic body into the space and thereby the hydrophilic solvent containing the microscopic body is further introduced into each of the receptacles via the opening to fill up the cavity of the receptacles;
a gas feeding unit configured to introduce gas into the space to substitute the hydrophilic solvent containing the microscopic body in the space by the gas and thereby disconnect fluid connection via the space between the receptacles leaving the hydrophilic solvent containing the microscopic body filled up in the cavity of the receptacles; and
a detector that detects the microscopic body present in the receptacles optically, electrically, and/or magnetically;
wherein the hydrophilic solvent further contains a hydratable substance selected from the group consisting of a gel, a hydrophilic polymer, and an osmolyte.

18. The substance detection device according to claim 17, wherein:

the gel is selected from the group consisting of agarose and acrylamide;

the hydrophilic polymer is selected from the group consisting of polyethylene glycol and cellulose; and the osmolyte is selected from the group consisting of glycine, betaine, sorbitol, sucrose, mannitol, trehalose, and urea.

19. The substance detection device according to claim 18, wherein the hydratable substance is contained in the hydrophilic solvent at a concentration of about 0.1 to 5%.

20. The substance detection device according to claim 17, wherein the hydratable substance is the gel or the hydrophilic polymer.

21. A method of detecting a microscopic body stored in a plurality of receptacles formed separately from each other, the method comprising the steps of:

(1) providing a substrate that includes
   a first layer part in which the plurality of receptacles for storing the microscopic body are formed by a plurality of sidewalls separating the respective receptacles from each other, and
   a second layer part facing the first layer part, thereby forming a space in between with the first layer part, the space connecting the plurality of receptacles;

(2) introducing a hydrophilic solvent containing the microscopic body into the space, and thereby the hydrophilic solvent containing the microscopic body is further introduced into each of the receptacles to fill cavities of the receptacles;

(3) introducing gas into the space to substitute the hydrophilic solvent containing the microscopic body in the space by the gas until fluid connection via the space between the receptacles is disconnected while the hydrophilic solvent containing the microscopic body remains filled in the receptacles; and (4) detecting the microscopic body present in the receptacles optically, electrically, and/or magnetically;

wherein the method further comprises the step of transpiration suppressing for suppressing transpiration of the hydrophilic solvent that fills the cavities of the receptacles during the detecting step by a hydratable substance contained in the hydrophilic solvent, wherein the hydratable substance is a gel, a hydrophilic polymer, or an osmolyte.

22. The method according to claim 21, wherein:

the gel is selected from the group consisting of agarose and acrylamide;

the hydrophilic polymer is selected from the group consisting of polyethylene glycol and cellulose; and the osmolyte is selected from the group consisting of glycine, betaine, sorbitol, sucrose, mannitol, trehalose, and urea.

23. The method according to claim 22, wherein the hydratable substance is contained in the hydrophilic solvent at a concentration of about 0.1 to 5%.

24. The method according to claim 21, wherein the hydratable substance is the gel or the hydrophilic polymer.

25. A substance detection device comprising:
   a substrate that includes
      a first layer part in which a plurality of receptacles for storing a microscopic body are formed by a plurality of sidewalls separating the respective receptacles from each other, and
      a second layer part facing the first layer part, thereby forming a space in between with the first layer part, the space connecting the plurality of receptacles;
   a liquid feeding unit that introduces a hydrophilic solvent containing the microscopic body into the space and thereby the hydrophilic solvent containing the microscopic body is further introduced into each of the receptacles to fill up cavities of the receptacles;
   a gas feeding unit configured to introduce gas into the space to substitute the hydrophilic solvent containing the microscopic body in the space by the gas until fluid connection via the space between the receptacles is disconnected while the hydrophilic solvent containing the microscopic body remains filled in the receptacles; and
   a detector that detects the microscopic body present in the receptacles optically, electrically, and/or magnetically;
   wherein the hydrophilic solvent further contains a hydratable substance selected from the group consisting of a gel, a hydrophilic polymer, and an osmolyte.

26. The substance detection device according to claim 25, wherein:

the gel is selected from the group consisting of agarose and acrylamide;

the hydrophilic polymer is selected from the group consisting of polyethylene glycol and cellulose; and the osmolyte is selected from the group consisting of glycine, betaine, sorbitol, sucrose, mannitol, trehalose, and urea.

27. The substance detection device according to claim 26, wherein the hydratable substance is contained in the hydrophilic solvent at a concentration of about 0.1 to 5%.

28. The substance detection device according to claim 25, wherein the hydratable substance is the gel or the hydrophilic polymer.

* * * * *